Figure 1:
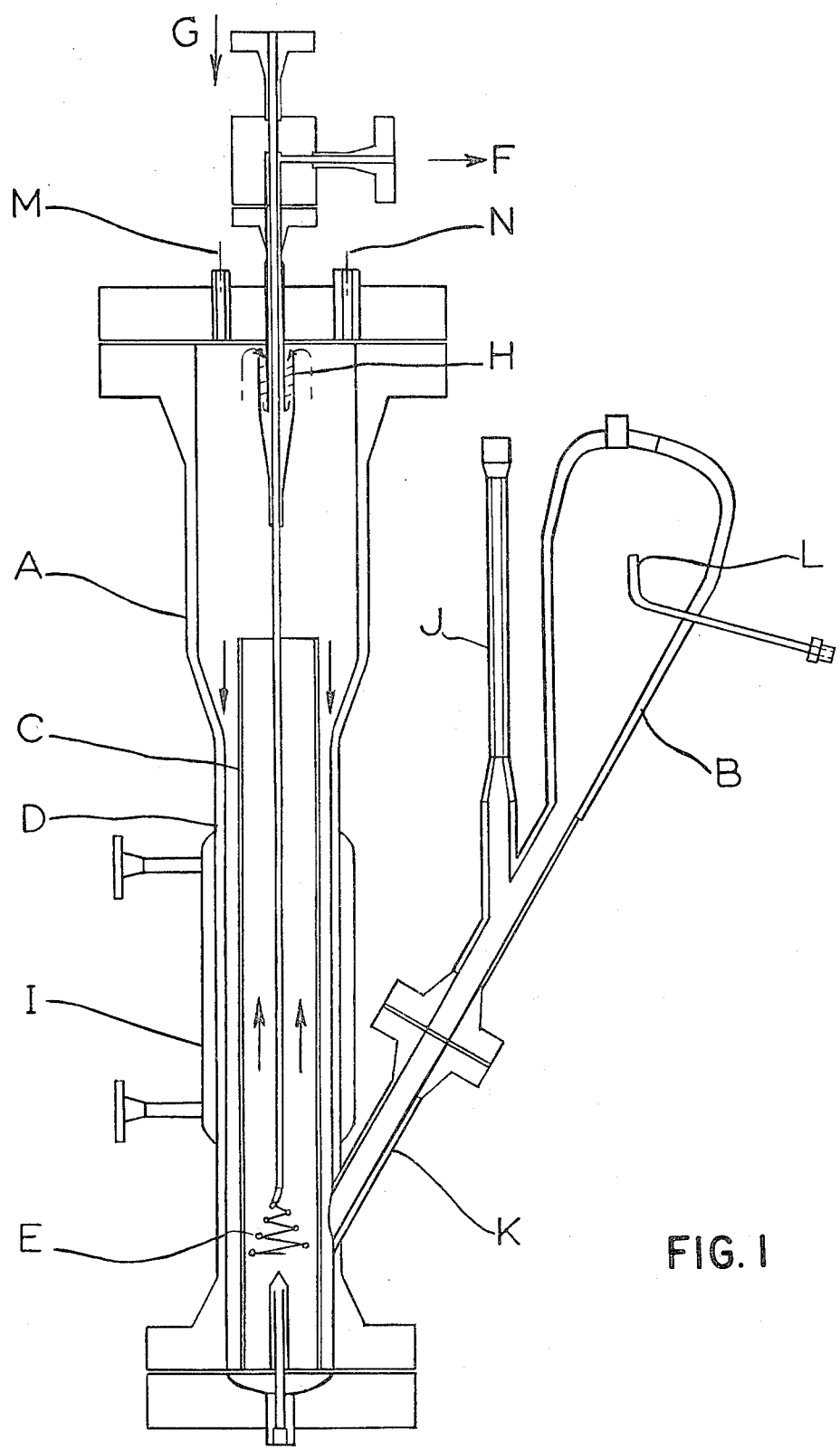

United States Patent [19]

Masotti et al.

[11] 4,111,662
[45] Sep. 5, 1978

[54] ARRANGEMENT FOR PREPARING ALKYLALUMINUMS

[75] Inventors: Robert Masotti, Lyon; Georges Biola, Venissieux; Henri Guerpillon, Saint-Cyr Au Mont d'Or, all of France

[73] Assignee: Rhone-Poulenc Industries, Paris, France

[21] Appl. No.: 699,338

[22] Filed: Jun. 24, 1976

[30] Foreign Application Priority Data

Jun. 27, 1975 [FR] France .............................. 75 20254

[51] Int. Cl.$^2$ .............................. C07F 5/06; B01J 8/22
[52] U.S. Cl. .............................. 422/231; 260/448 A; 260/448 R; 261/77; 261/124; 422/233
[58] Field of Search ....................... 260/448 A, 448 R; 23/283, 285, 260, 262; 261/77, 124

[56] References Cited
U.S. PATENT DOCUMENTS

| | | | |
|---|---|---|---|
| 2,576,769 | 11/1957 | Avedikian | 23/260 X |
| 3,373,179 | 3/1968 | Lewis | 260/448 A |
| 3,388,142 | 6/1968 | Cameron et al. | 260/448 A |
| 3,759,669 | 9/1973 | Aaron et al. | 23/283 X |

Primary Examiner—James H. Tayman, Jr.
Attorney, Agent, or Firm—McDougall, Hersh & Scott

[57] ABSTRACT

A single-stage reactor in the form of two concentric tubes and, one acting as a central stack and the other as a wall of reactor, widening out towards the top; a gas diffuser at the bottom of the stack, enabling gas to be injected into the liquid column above the diffuser, while a vesicle remover is located in the upper part of reactor; pipes and for feeding in the reagents, and a pipe for forcing back the gaseous phase at the top of reactor; a connection inclined by over 45° to an extension of the horizontal and establishing direct communication between the bottom of reactor and a decanting chamber; and a vertical degassing tube located between connection and decanting chamber.

Application of this arrangement to the reaction between finely divided aluminum, hydrogen and at least one olefin having 2 to 30 carbon atoms, at a temperature of from 100° to 200° and a pressure of 30 to 200 bars, in a perfectly homogeneous medium for the preparation of alkylaluminums.

7 Claims, 2 Drawing Figures

ARRANGEMENT FOR PREPARING ALKYLALUMINUMS

The invention relates to a process whereby finely divided solids are continuously introduced into reaction with liquids and gases; more particularly, it concerns the preparation of alkylaluminums.

It is known that alkylaluminums can be prepared from aluminum, hydrogen and olefins as described in the Karl Ziegler patents for the preparation of the well known Ziegler type catalysts, by the following reactions:

$$Al + 3/2\, H_2 + 2\, Al\, R_3 \rightarrow 3\, Al\, R_2 H \qquad (1)$$

$$3\, Al\, R_2 H + 3\, R= \rightarrow 3\, Al\, R_3 \qquad (2)$$

wherein R represents an alkyl (alcoyle) group having 2 to 30 carbon atoms and R= is the α-olefin corresponding to the alkyl radical R.

It is also known that trialkylaluminum Al $R_3$ may be prepared either in two successive stages in separate reactors - monohydride of dialkylaluminum being prepared in a first reactor in accordance with reaction (1) above, and trialkyl-aluminum being prepared in a second reactor in accordance with reaction (2), with the trialkylaluminum being recycled into the first reactor - or in a single stage in one reactor.

The two-stage process generally enables a better yield to be obtained than the single stage process. However, it has the disadvantage of requiring a multiplicity of reactors and thus a complex installation, and recycling the alkylaluminum, which entails circulating large quantities of dangerous liquids at high pressures.

Various arrangements have already been described for preparing dialkylaluminum monohydride, a reaction which involves contact between the three phases, gases, liquids and solids. They are particularly described in U.S. Pat. No. 3,373,179 and French Pat. No. 1,420,392 of Continental Oil Company, French Pat. No. 1,173,100 of Studiengesellschaft Kohle and Belgian Pat. No. 546,432 of Karl Ziegler.

However, the arrangements for continuous reaction described in these patents have some disadvantages, the most serious of which are the following:

- some, e.g. French Pat. No. 1,173,100, use a system of sieving or filtering trays with gas cushions interposed to improve contact. This system may be the source of partial clogging or blocking of the reactor by very active particles of aluminum. These tend to agglomerate due to the absence of any isolating or protective film of alumina, with all the difficulties which this creates in view of the dangerous nature of alkylaluminums;

- others, e.g. French Pat. No. 1,420,392, use a mechanical agitation system inside the reactor, which may comprise one or more stages, with the mechanical difficulties which this involves in obtaining imperviousness in the passage for the drive-shaft, since the reaction pressure is high (from 35 to 175 bars). There are also problems connected with erosion of the internal blades, sintering of active aluminum on the rotating passages and re-suspension of the deposits of aluminum particles forced by decantation.

The object of this invention is a method of preparing a mixture of monohydride of dialkylaluminums and trialkyl-aluminums with a good yield, in a single stage and a single reaction zone. The reaction zone is made perfectly homogeneous by the effectiveness of complete contact provided therein between the three phases gas, liquid and solid, thus enabling all the above-mentioned disadvantages to be avoided.

Another object of the invention includes an arrangement comprising a compact reactor capable of promoting a reaction in a perfectly homogeneous medium, in which excellent circulation and a very intimate mixture of the reagents allow for very good contact between the various phases present. This ensures a marked improvement in the kinetics of the generally slow reaction of alkylating aluminum and in the kinetics of desired heat exchanges. The arrangement also enables the following operations to be carried out simultaneously and continuously: decantation of the non-reacted aluminum outside the reactor proper, before the liquid phase is drawn off; return of the non-reacted aluminum straight to the reactor without using any pump or lock; and drawing-off of the liquid phase containing the alkyl aluminums produced at the same time as the very fine impurities, which are present in the powdered aluminum from the outset and necessary to give the metal an appropriate action.

In the method of preparing a mixture of monohydride of alkylaluminums and trialkylaluminums according to the invention, gaseous hydrogen, aluminum in the form of fine particles and at least one olefin having 2 to 30 carbon atoms are reacted at a pressure of 30 to 200 bars, preferably 80 to 150 bars, and a temperature of 100° to 200° C. The method is characterized in that hydrogen and/or an inert gas is injected into a single stage single reaction zone, into a reaction medium comprising the three phases, solid, liquid and gas, at the bottom of the reaction zone, in the presence of a stack immersed in the reaction medium, thus enabling the reagents to be brought into contact by circulation of the three phases, gas, liquid and solid, in two liquid columns by the gas-lift method. The resultant reaction product is let into a decanting zone through an opening provided in the lower part of the reaction zone communicating directly with a lower part of the decanting zone. The liquid mixture of monohydride of dialkyluminums and trialkyluminums, freed from the particles of non-reacted aluminum, is drawn off and collected by overflowing the upper part of the decanting zone, while the non-reacted aluminum, which has been decanted near the said opening, is recycled by being carried into the reaction zone by the said circulation of the reaction medium.

The hydrogen and/or an inert gas may be injected outside the stack, into the annular space defined by the stack immersed in the reaction medium and the periphery of the reaction zone.

However, in accordance with the preferred practice of this invention, the hydrogen and/or an inert gas is injected inside the stack. The three phases of the reaction medium are then set into circulation by the same method as with injection outside the above-mentioned stack, except that the direction in which the reaction medium circulates is reversed.

The continuous circulating movement of the three phases present, solid, liquid and gas, makes it possible to obtain excellent agitation of the reaction medium and actual formation of a perfectly homogeneous reaction zone.

In one embodiment of the invention, the liquid mixture of monohydride of dialkyluminums and trialkyluminums is drawn off from the decanting zone so that its overflow level controls the level of the reaction medium in the reaction zone. In a preferred embodiment, the overflow level of the decanting zone is set to the same level as that of the reaction zone.

The flow rate at which the hydrogen and/or an inert gas, such as nitrogen or argon, are injected at the bottom of the reaction zone depends on the circulating rates of the reactive liquid required to carry the particles of aluminum; these may be of various sizes, e.g. with a grain size distribution ranging from a few microns to a few millimeters.

According to the invention, it is appropriate to pass the gas phase located above the reactive liquid in circulation into a vesicle-removing zone (zone for eliminating small particles of liquid carried by the gas phase). The gas phase, thus freed of liquid, may undergo a treatment such as condensation, cooling, heating and/or purging before being compressed and returned to the bottom of the reaction zone.

It has been found that, in order to increase the effectiveness of decantation, it is advantageous for the lower part of the decanting zone, which communicates directly with the reaction zone, to have a cross-section less than that of its upper portion. Thus a calm zone tends to form at the top of the decanting zone whereas the bottom is subject to slight turbulence created by the circulating reagents, particularly in the immediate vicinity of the opening connecting the two adjoining decanting and reaction zones. The zone of turbulence also promotes sliding of the particles of decanted aluminum along the wall for return to the reaction medium.

One feature of the invention is that the lower part of the decanting zone is inclined by an angle of over 45° to the horizontal. Applicants have found that effective decantation of the particles of non-reacted aluminum increases if the inclination is at least 60°.

It may happen that gas bubbles, carried along with the liquid in circulation, ascend into the decanting zone and destroy its balance. In order to avoid this drawback, it is advantageous to interpose a vertical zone, located between the upper and lower part of the decanting zone, to trap the bubbles rising into the decanting zone.

The invention may be applied very satisfactorily to the preparation of butylaluminums (n-butyl, secondary-butyl and isobutylaluminum) by the method described in the application filed concurrently herewith in the name of Emile Trebillon and entitled "Method of Obtaining Straight-Chain Primary Alcohols From $C_4$ Hydrocarbon Cuts".

The arrangement for preparing alkylaluminum according to the invention comprises a single stage reactor consisting of an external jacket widening out at the top, a central stack inside the reactor with a gas diffuser at the bottom; a decanter outside the reactor, comprising a joint or junction which connects it directly to the lower part of the reactor, a chamber of relatively large section to create a calm zone for decanting solid particles, and possibly a vertical tube to trap the gas bubbles ascending through the joint.

Figure 2:
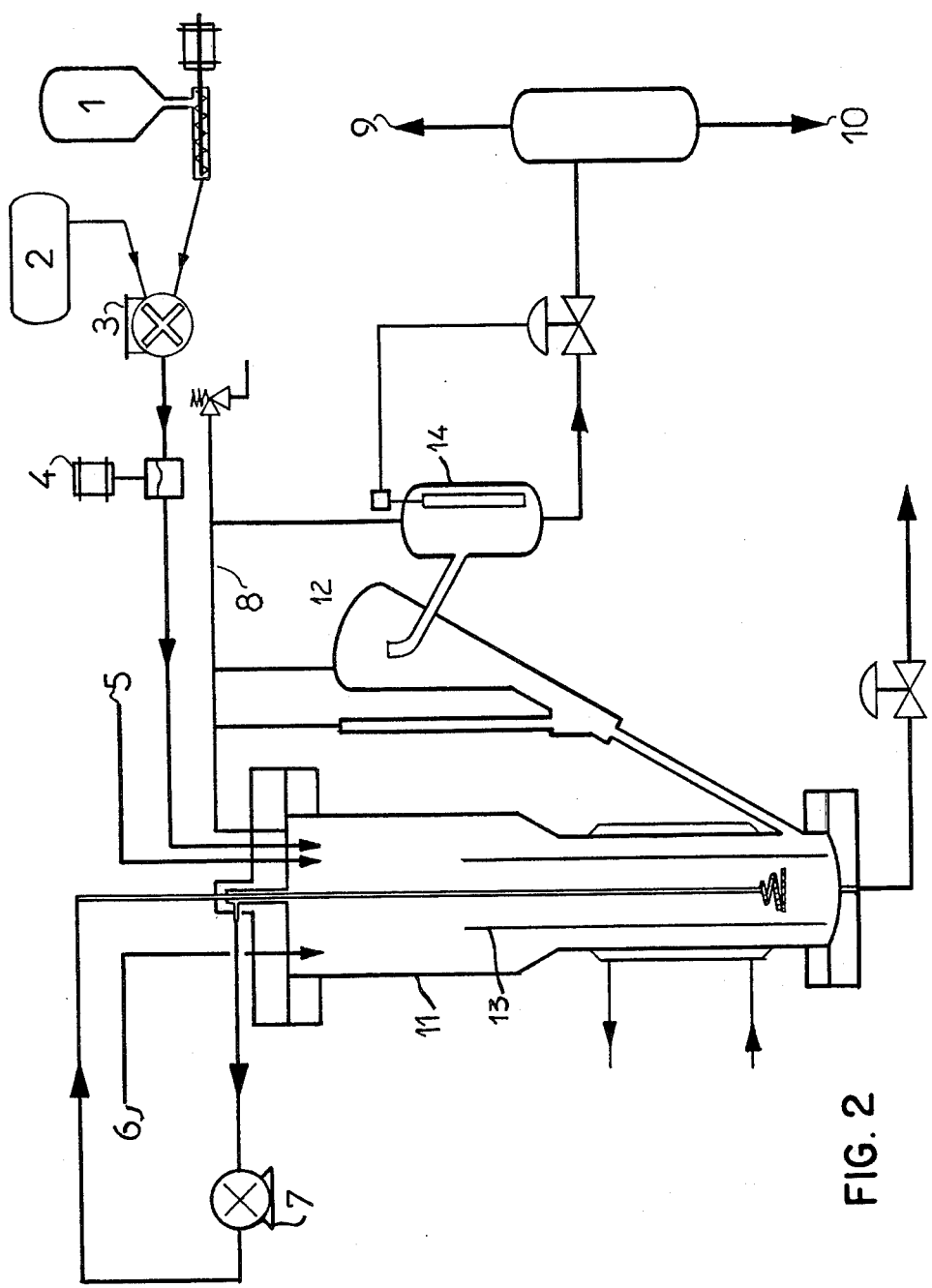

In the accompanying drawings:

FIG. 1 is a schematic sectional elevational view of an arrangement according to the invention; and FIG. 2 is a flow diagram of an installation which makes use of the arrangement of FIG. 1 for preparing alkylaluminums according to the invention, as illustrated in the following working example.

In FIG. 1, the reactor proper, referred to as A, is of the gas-lift type. Introduction of gas into the liquid phase of the reaction medium creates differences in density, and circulation may be induced as a result of this variation.

The rate at which the liquid phase is circulated must be sufficient to keep the solid phase in suspension. The solid phase may be in the form of powder, granules, aluminum chips or generally in finely divided form.

For this purpose reactor A and stack C consist of two concentric tubular members, such that the internal section of stack C is approximately equal to the section of the annular space thus formed.

In a special embodiment of the invention, a gas diffuser or injector E is provided inside stack C and preferably at the bottom of the stack. The diffuser or injector emits gaseous bubbles into the central column of liquid, causing the reagents to be circulated, as by an upward flow in the stack, and the solid phase put into suspension.

According to the invention, the peripheral tube of reactor A widens out towards the top. The purpose of this is to enable the liquid overflowing the central stack to be degassed, thus reducing the recycling of bubbles.

The top of reactor A proper receives pipes M and N for the introduction of raw materials: hydrogen, divided aluminum, olefins and possibly appropriate solvents of known types. The pipes may descend into the reaction medium or simply open into the gaseous zone of the reactor as shown in FIG. 1. The introduced reagents are immediately caught up in the circulating reaction medium and mixed intimately with the other reagents.

The gas diffuser may be of very varied designs, selected from known systems such as inter alia a metallic sintered member, a perforated plate or tube, or a nozzle.

The diffuser may be supplied through G with reactive gas from an external source, possibly diluted with an inert gas, and/or via a gas circulator of compressor located between F and G and not shown in FIG. 1. The circulator or compressor would draw the gas phase from the top of the reactor, at F, recirculate it at G into the tube connected to diffuser E at the bottom of the reactor.

It may be helpful to place a vesicle remover H (a system for eliminating small particles of liquid carried by the gas phase) at the top of reactor A. The gas phase located above the circulacting reactive liquid then passes through the vesicle remover before emerging at F and being forced back at G into the tube connected to diffuser E, as described.

The desired thermal balance in reactor A is provided with the aid of a double external jacket I. However, any other appropriate means may be applied such as inter alia a coiled heat exchange tube inside the reactor through which a heat exchange fluid is circulated, or by cooling, heating or condensing gases outside the reactor.

The other part of the arrangement, according to the invention, comprises a decanter B directly connected to the annular portion of reactor A by a tube K. The decanter generates a calm zone in which solid-liquid separation can take place. A section of the upper part of decanter B is chosen so that the desired degree of separation is obtained.

According to the invention, tube K is inclined by over 45° and preferably by about 60° to 65° to the horizontal. Angles of inclination over 65°, e.g. angles of 80°, may be used, but such arrangements are not easy to construct in practice, and applicants have found that the larger angles of inclination have the disadvantage of upsetting the calm zone sought to be established in decanter B.

In the course of decantation, the solids which settle in inclined tube K descend the tube and are put back into circulation as soon as they reach the annular portion of the reactor.

Decanter B operates substantially at a constant level, the liquid containing the mixture of monohydride or dialkylaluminums and trialkylaluminums produced being drawn off through an overflow, e.g. by means of a drawing-off tube L. The height at which the liquid is drawn off or the level at which it overflows governs the height or level of liquid in reactor A.

It is helpful to place a degassing tube J in the upper portion of tube K in advance of decanter B so as to trap the bubbles which are carried into the annular zone of reactor A and may otherwise rise into the decanter and destroy its balance.

Since the arrangement has to operate at high pressure for the preparation of alkylaluminums, gas counterpoise lines (not shown in FOG. 1) connect reactor A degassing tube J and decanter B.

The arrangement, according to the invention, has the advantage of being very simple in internal construction, since it has no shaft passing through it, no mechanical agitating system, no filtering sieves, no plates and no screens or baffles. This represents a series of very important technical advantages, considering that the reaction pressure is high, e.g. at 80 to 175 bars, that alkylaluminums, being pyrophoric, are tricky products to handle, and that the aluminum in circulation is in a highly divided and activated state and may easily clog the interior of a complex reactor like those of prior art and easily be sintered on mechanical components undergoing friction or rotation.

The arrangement according to the invention enables the very fine impurities, which are originally present in the powdered aluminum and necessary to give the metal a suitable action, to be drawn off at the same time as the liquid.

The type of reactor described above also permits excellent circulation and intimate mixing of the reagents, thus providing for very satisfactory mass transfer kinetics and the desired heat exchanges.

In general, the arrangement of the invention may be used to carry out other types of reaction, simultaneously involving the three phases present, solid, liquid and gas, and requiring intimate contact between the three phases. Special examples of such reactions are catalytic hydrogenation in the liquid phase and water-treatment of petroleum fractions.

Since the arrangement is intended, more generally, to provide triple contact between gases, liquids and solids, it comprises, according to the invention, a reactor and a decanter and is characterized in that the reactor comprises a single-stage reactor in the form of two concentric tubes, one acting as a central stack and the other as a reactor wall which widens out towards the top; at the bottom of the stack is a gas diffuser enabling gas to be injected into the liquid column above the diffuser and thereby causing the reagents to be put into circulation by the gas-lift method, in the absence of any mechanical agitating system. The reactor communicates directly with the decanter by a connection, such as a tube, which is inclined by an angle of over 45° and preferably by at least 60° to the horizontal; the connection leading to a decanting chamber located in the upper part of the decanter, the upper part being of appropriate cross-section, depending on the grain-size distribution of the particles of solids to be decanted.

In a preferred embodiment, the inclined connection is provided with a vertical tube located between the decanting chamber and the place where the decanter is joined to the reaction, so as to trap bubbles coming from the reactor, while the top of the inside of the reactor contains a vesicle remover effective to draw in the gas phase, e.g. by means of a system whereby the gas is drawn in and forced back outside the reactor.

The following example concerns the preparation of a mixture of tributylaluminums and monohydride of dibutylaluminums from hydrogen, divided aluminum and a $C_4$ hydrocarbon cut, and refers to the layout in FIG. 2. The sole purpose of the example is to illustrate and explain the operation of the process and arrangement according to the invention, and it should not be considered as imposing any restrictions on the invention.

The initial aluminum, in the form of granules, scales or chips in a hopper (1), and a hydrocarbon cut originating from a cracked petroleum fraction, contained in a tank (2) having the following composition, in percent by weight.

1-butene: 53.9% 2-butene: 28.6% isobutene: 7.2%
butane: 8.7% isobutane: 1.5% butadiene: 0.05%
are fed into a grinding mill (3).

The grinding of the aluminum in a liquid medium enables the metal particles to be reduced in size and activated before being fed into reactor (11).

The finely divided aluminum slurry in the $C_4$ hydrocarbon cut is then pumped into reactor (11) by means of a pump (4). Hydrogen, which is introduced through a pipe (5), enables a constant pressure to be maintained in the reactor. The reactor is designed to resist high pressures (up to 200 bars). Inside the reactor is a central stack (13), at the bottom of which is a bubble generator, provided as a gas diffuser, which is fed by means of a blower (7) which withdraws the gas phase at the top of the reactor and forces it back at the bottom of the reactor through the diffuser, thus putting the reagents into circulation.

About the outer walls of reactor (11), a double jacket control is provided to the temperature of the reaction mixture by application or removal of heat.

The reactor is also equipped with a pipe (6) for introducing solvent, e.g. rinsing solvent, and further comprises counterpoise lines (8) for the gas phases in the other parts of the arrangement, with the usual safety systems, such as a valve and a breaker disc.

The proportions (by weight) of reagents continuously injected into the reactor for synthesizing butylaluminums (mixtures of tributylaluminums and monohydrides of dibutylaluminums) are as follows, per hour:
aluminum: 104 parts hydrogen: 13 parts
$C_4$ cut described above: 656 parts
The reaction is carried out at 140° C and a pressure of 120 bars.

As soon as the raw materials are fed into reactor (11), they are immediately mixed with the circulating reaction medium.

The rate at which the reagents are introduced is controlled so as to keep the molar proportion of monohydride of dibutylaluminums (which can be measured by complexometry with isoquinoline) at 56% in the butylaluminums. The quantity of the monohydride is controlled by the ratio of the quantity of aluminum supplied in (1) to the quantity of $C_4$ cut supplied in (2).

The unreacted aluminum in the reaction medium is decanted in decanter (12), and a liquid phase freed from the metal particles of aluminum, but charged with very fine impurities known as sludges, is drawn off into a vessel (14) with a constant level. The liquid drawn off, which corresponds to the liquid which overflows the drain tube in the decanter, is then expanded to atmospheric pressure, enabling the gases resulting from expansion to be recovered at (9). These chiefly comprise hydrogen and 136 parts by weight of $C_4$ hydrocarbons having the following composition:

1-butene: 4.4% 2-butene: 15.5%
isobutene: 2.9% butane + isobutane: 77.1%

The liquid, essentially consisting of 635 parts by weight of a mixture of tributylaluminums and monohydrides of dibutylaluminums comprising 81% of n-butyl radicals, 11% of sec-butyl radicals and 8% of isobutyl radicals, is collected at (10).

We claim:

1. Apparatus for preparing alkylaluminums comprising a single stage reactor formed of an outer tubular member and an inner tubular member concentrically arranged within the outer tubular member with an annular space in between, the outer tubular member having a portion of increasing diameter in the area above the inner tubular member, a gas diffuser in communication with the bottom portion of the inner tubular member and means for introducing a gas through the diffuser into the interior of the inner tubular member whereby liquid filling the inner tubular member is put into circulation by the gas-lift methods, inlets for feeding hydrogen, aluminum particles and olefins having 2 to 30 carbon atoms into the upper portion of the reactor, an outlet in communication with the upper portion of the reactor for the removal of gases, a decanter having a quiescent zone for decanting solid particles, a passage extending at an angle greater than 45° with the horizontal communicating the decanter with the annular space in the bottom portion of the reactor for the flow of liquid therebetween, and an overflow in the decanter, at a level above the upper end of the inner tubular member which operates to control the level of liquid in the decanter and reactor.

2. Apparatus as claimed in claim 1 which includes a means within the upper portion of the reactor in communication with the gas outlet for separating entrained liquid from the gas before issuance of the gas from the outlet.

3. Apparatus as claimed in claim 1 which includes a tube extending upwardly from the inclined passage between the decanter and reactor for removal of gas from the fluid flowing through the passage.

4. Apparatus as claimed in claim 1 in which the passage is inclined at an angle of 60° to 65° to the horizontal.

5. Apparatus as claimed in claim 1 in which the passage comprises an elongate tubular member and the decanter comprises a chamber of relatively large dimension communicating with the upper end of the tubular member.

6. Apparatus for producing triple contact between gases, liquids and solids comprising a reactor and a decanter, characterized in that the reactor is a single-stage reactor in the form of an outer tubular member and an inner tubular member concentrically arranged within the outer tubular member with an annular space in between, the outer tubular member having a portion of increasing diameter in the area above the upper end of the inner tubular member a gas diffuser in communication with the bottom portion of the inner tubular member to enable a gas to be injected into the column of liquid above the diffuser in the inner tubular member thereby to enable the reagents to be put into circulation by a gas-life concept, an outlet in communication with the enlarged portion of the outer tubular member for the removal of separated gases, a decanter in communication with the lower end portion of the outer tubular member for flow of liquid therethrough and return of separated solids, and means for removal of liquid free of solids from the decanter at a level above the upper end of the inner tubular member.

7. Apparatus as claimed in claim 6 in which the connection is inclined at an angle of at least 60° with the horizontal.

* * * * *

UNITED STATES PATENT OFFICE
CERTIFICATE OF CORRECTION

Patent No. 4,111,662          Dated September 5, 1978

Inventor(s) Robert Masotti et al.

It is certified that error appears in the above-identified patent and that said Letters Patent are hereby corrected as shown below:

Column 5, line 8, after "monohydride change "or" to -- of --

Signed and Sealed this

First Day of May 1979

[SEAL]

Attest:

RUTH C. MASON
Attesting Officer

DONALD W. BANNER
Commissioner of Patents and Trademarks